(12) United States Patent
Ostroff

(10) Patent No.: US 9,272,155 B2
(45) Date of Patent: Mar. 1, 2016

(54) LEADLESS CARDIAC PACEMAKER WITH SECONDARY FIXATION CAPABILITY

(71) Applicant: Nanostim, Inc., Sunnyvale, CA (US)

(72) Inventor: Alan Ostroff, Pleasanton, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 13/967,180

(22) Filed: Aug. 14, 2013

(65) Prior Publication Data
US 2015/0297899 A1    Oct. 22, 2015

Related U.S. Application Data

(63) Continuation of application No. 12/698,969, filed on Feb. 2, 2010, now Pat. No. 8,527,068.

(60) Provisional application No. 61/149,176, filed on Feb. 2, 2009, provisional application No. 61/155,038, filed on Feb. 24, 2009.

(51) Int. Cl.
*A61N 1/372* (2006.01)
*A61N 1/375* (2006.01)
*A61N 1/05* (2006.01)

(52) U.S. Cl.
CPC ............ *A61N 1/3756* (2013.01); *A61N 1/0573* (2013.01); *A61N 1/375* (2013.01)

(58) Field of Classification Search
CPC ..... A61N 1/057; A61N 1/0573; A61N 1/059; A61N 1/37205; A61N 1/3756
See application file for complete search history.

(56) References Cited

U.S. PATENT DOCUMENTS

| | | | |
|---|---|---|---|
| 3,199,508 A | 8/1965 | Roth | |
| 3,212,496 A | 10/1965 | Preston | |
| 3,218,638 A | 11/1965 | Honig | |
| 3,241,556 A | 3/1966 | Zacouto | |
| 3,478,746 A | 11/1969 | Greatbatch | |

(Continued)

FOREIGN PATENT DOCUMENTS

| | | |
|---|---|---|
| EP | 1741465 A1 | 1/2007 |
| JP | H04-506167 A | 10/1992 |

(Continued)

OTHER PUBLICATIONS

U.S. Appl. No. 10/891,747 entitled "System and method for synchronizing supplemental pacing pulses generated by a satellite pacing device with primary pulses delivered by a separate pacing device," filed Jul. 14, 2004 (abandoned prior to pub.: CIP of this app. is U.S. Pat. 7,630,767).

(Continued)

*Primary Examiner* — Allen Porter, Jr.
(74) *Attorney, Agent, or Firm* — Theresa A. Raymer

(57) ABSTRACT

The invention relates to leadless cardiac pacemakers (LBS), and elements and methods by which they affix to the heart. The invention relates particularly to a secondary fixation of leadless pacemakers which also include a primary fixation. Secondary fixation elements for LBS's may passively engage structures within the heart. Some passive secondary fixation elements entangle or engage within intraventricular structure such as trabeculae carneae. Other passive secondary fixation elements may engage or snag heart structures at sites upstream from the chamber where the LBS is primarily affixed. Still other embodiments of passive secondary fixation elements may include expandable structures.

19 Claims, 6 Drawing Sheets

(56) References Cited

U.S. PATENT DOCUMENTS

| | | |
|---|---|---|
| 3,603,881 A | 9/1971 | Thornton |
| 3,727,616 A | 4/1973 | Lenzkes |
| 3,757,778 A | 9/1973 | Graham |
| 3,823,708 A | 7/1974 | Lawhorn |
| 3,830,228 A | 8/1974 | Foner |
| 3,835,864 A | 9/1974 | Rasor et al. |
| 3,836,798 A | 9/1974 | Greatbatch |
| 3,870,051 A | 3/1975 | Brindley |
| 3,872,251 A | 3/1975 | Auerbach et al. |
| 3,905,364 A | 9/1975 | Cudahy et al. |
| 3,940,692 A | 2/1976 | Neilson et al. |
| 3,943,926 A | 3/1976 | Barragan |
| 3,946,744 A | 3/1976 | Auerbach |
| 3,952,750 A | 4/1976 | Mirowski et al. |
| 4,027,663 A | 6/1977 | Fischler et al. |
| 4,072,154 A | 2/1978 | Anderson et al. |
| 4,083,366 A | 4/1978 | Gombrich et al. |
| 4,102,344 A | 7/1978 | Conway et al. |
| 4,146,029 A | 3/1979 | Ellinwood, Jr. |
| 4,151,513 A | 4/1979 | Menken et al. |
| 4,151,540 A | 4/1979 | Sander et al. |
| 4,152,540 A | 5/1979 | Duncan et al. |
| 4,173,221 A | 11/1979 | McLaughlin et al. |
| 4,187,854 A | 2/1980 | Hepp et al. |
| 4,210,149 A | 7/1980 | Heilman et al. |
| RE30,366 E | 8/1980 | Rasor et al. |
| 4,223,678 A | 9/1980 | Langer et al. |
| 4,250,888 A | 2/1981 | Grosskopf |
| 4,256,115 A | 3/1981 | Bilitch |
| 4,296,756 A | 10/1981 | Dunning et al. |
| 4,310,000 A | 1/1982 | Lindemans |
| 4,318,412 A | 3/1982 | Stanly et al. |
| 4,336,810 A | 6/1982 | Anderson et al. |
| 4,350,169 A | 9/1982 | Dutcher et al. |
| 4,374,382 A | 2/1983 | Markowitz |
| 4,406,288 A | 9/1983 | Horwinski et al. |
| 4,411,271 A | 10/1983 | Markowitz |
| 4,418,695 A | 12/1983 | Buffet |
| 4,424,551 A | 1/1984 | Stevenson et al. |
| 4,428,378 A | 1/1984 | Anderson et al. |
| 4,440,173 A | 4/1984 | Hudziak et al. |
| 4,442,840 A | 4/1984 | Wojciechowicz, Jr. |
| 4,453,162 A | 6/1984 | Money et al. |
| 4,458,692 A | 7/1984 | Simson |
| 4,481,950 A | 11/1984 | Duggan |
| 4,513,743 A | 4/1985 | van Arragon et al. |
| 4,516,579 A | 5/1985 | Irnich |
| 4,522,208 A | 6/1985 | Buffet |
| 4,524,774 A | 6/1985 | Hildebrandt |
| 4,531,527 A | 7/1985 | Reinhold, Jr. et al. |
| 4,543,955 A | 10/1985 | Schroeppel |
| 4,550,370 A | 10/1985 | Baker |
| 4,552,127 A | 11/1985 | Schiff |
| 4,552,154 A | 11/1985 | Hartlaub |
| 4,562,846 A | 1/1986 | Cox et al. |
| 4,586,508 A | 5/1986 | Batina et al. |
| 4,606,352 A | 8/1986 | Geddes et al. |
| 4,607,639 A | 8/1986 | Tanagho et al. |
| 4,612,934 A | 9/1986 | Borkan |
| 4,625,730 A | 12/1986 | Fountain et al. |
| 4,679,144 A | 7/1987 | Cox et al. |
| 4,681,111 A | 7/1987 | Silvian |
| 4,681,117 A | 7/1987 | Brodman et al. |
| 4,702,253 A | 10/1987 | Nappholz et al. |
| 4,719,920 A | 1/1988 | Alt et al. |
| 4,722,342 A | 2/1988 | Amundson |
| 4,750,495 A | 6/1988 | Moore et al. |
| 4,763,340 A | 8/1988 | Yoneda et al. |
| 4,763,655 A | 8/1988 | Wirtzfeld et al. |
| 4,787,389 A | 11/1988 | Tarjan |
| 4,791,931 A | 12/1988 | Slate |
| 4,793,353 A | 12/1988 | Borkan |
| 4,794,532 A | 12/1988 | Leckband et al. |
| 4,802,481 A | 2/1989 | Schroeppel |
| 4,809,697 A | 3/1989 | Causey, III et al. |
| 4,827,940 A | 5/1989 | Mayer et al. |
| 4,830,006 A | 5/1989 | Haluska et al. |
| 4,844,076 A | 7/1989 | Lesho et al. |
| 4,846,195 A | 7/1989 | Alt |
| 4,858,610 A | 8/1989 | Callaghan et al. |
| 4,860,750 A | 8/1989 | Frey et al. |
| 4,875,483 A | 10/1989 | Vollmann et al. |
| 4,880,004 A | 11/1989 | Baker, Jr. et al. |
| 4,883,064 A | 11/1989 | Olson et al. |
| 4,886,064 A | 12/1989 | Strandberg |
| 4,896,068 A | 1/1990 | Nilsson |
| 4,903,701 A | 2/1990 | Moore et al. |
| 4,905,708 A | 3/1990 | Davies |
| 4,926,863 A | 5/1990 | Alt |
| 4,974,589 A | 12/1990 | Sholder |
| 4,987,897 A | 1/1991 | Funke |
| 4,995,390 A | 2/1991 | Cook et al. |
| 5,010,887 A | 4/1991 | Thornander |
| 5,012,806 A | 5/1991 | De Bellis |
| 5,014,701 A | 5/1991 | Pless et al. |
| 5,040,533 A | 8/1991 | Fearnot |
| 5,040,534 A | 8/1991 | Mann et al. |
| 5,040,536 A | 8/1991 | Riff |
| 5,042,497 A | 8/1991 | Shapland |
| 5,052,399 A | 10/1991 | Olive et al. |
| 5,058,581 A | 10/1991 | Silvian |
| 5,065,759 A | 11/1991 | Begemann et al. |
| 5,076,270 A | 12/1991 | Stutz, Jr. |
| 5,076,272 A | 12/1991 | Ferek-Petric |
| 5,085,224 A | 2/1992 | Galen et al. |
| 5,086,772 A | 2/1992 | Larnard et al. |
| 5,088,488 A | 2/1992 | Markowitz et al. |
| 5,095,903 A | 3/1992 | DeBellis |
| 5,109,845 A | 5/1992 | Yuuchi et al. |
| 5,111,816 A | 5/1992 | Pless et al. |
| 5,113,859 A | 5/1992 | Funke |
| 5,113,869 A | 5/1992 | Nappholz et al. |
| 5,133,350 A | 7/1992 | Duffin |
| 5,135,004 A | 8/1992 | Adams et al. |
| 5,170,784 A | 12/1992 | Ramon et al. |
| 5,170,802 A | 12/1992 | Mehra |
| 5,179,947 A | 1/1993 | Meyerson et al. |
| 5,184,616 A | 2/1993 | Weiss |
| 5,193,539 A | 3/1993 | Schulman et al. |
| 5,193,540 A | 3/1993 | Schulman et al. |
| 5,193,550 A | 3/1993 | Duffin |
| 5,217,010 A | 6/1993 | Tsitlik et al. |
| 5,247,945 A | 9/1993 | Heinze et al. |
| 5,259,394 A | 11/1993 | Bens |
| 5,267,150 A | 11/1993 | Wilkinson |
| 5,282,841 A | 2/1994 | Szyszkowski |
| 5,284,136 A | 2/1994 | Hauck et al. |
| 5,291,902 A | 3/1994 | Carman |
| 5,300,093 A | 4/1994 | Koestner et al. |
| 5,304,206 A | 4/1994 | Baker, Jr. et al. |
| 5,304,209 A | 4/1994 | Adams et al. |
| 5,313,953 A | 5/1994 | Yomtov et al. |
| 5,318,596 A | 6/1994 | Barreras et al. |
| 5,331,966 A | 7/1994 | Bennett et al. |
| 5,333,095 A | 7/1994 | Stevenson et al. |
| 5,336,244 A | 8/1994 | Weijand |
| 5,342,401 A | 8/1994 | Spano et al. |
| 5,354,317 A | 10/1994 | Alt |
| 5,358,514 A | 10/1994 | Schulman et al. |
| 5,373,852 A | 12/1994 | Harrison et al. |
| 5,383,912 A | 1/1995 | Cox et al. |
| 5,383,915 A | 1/1995 | Adams |
| 5,404,877 A | 4/1995 | Nolan et al. |
| 5,405,367 A | 4/1995 | Schulman et al. |
| 5,406,444 A | 4/1995 | Selfried et al. |
| 5,411,532 A | 5/1995 | Mortazavi |
| 5,411,535 A | 5/1995 | Fujii et al. |
| 5,411,537 A | 5/1995 | Munshi et al. |
| 5,417,222 A | 5/1995 | Dempsey et al. |
| 5,419,337 A | 5/1995 | Dempsey et al. |
| 5,431,171 A | 7/1995 | Harrison et al. |
| 5,446,447 A | 8/1995 | Carney et al. |
| 5,456,261 A | 10/1995 | Luczyk |
| 5,466,246 A | 11/1995 | Silvian |

(56) References Cited

U.S. PATENT DOCUMENTS

| | | |
|---|---|---|
| 5,469,857 A | 11/1995 | Laurent et al. |
| 5,480,415 A | 1/1996 | Cox et al. |
| 5,481,262 A | 1/1996 | Urbas et al. |
| 5,522,876 A | 6/1996 | Rusink |
| 5,531,779 A | 7/1996 | Dahl et al. |
| 5,531,781 A | 7/1996 | Alferness et al. |
| 5,531,783 A | 7/1996 | Giele et al. |
| 5,539,775 A | 7/1996 | Tuttle et al. |
| 5,549,654 A | 8/1996 | Powell |
| 5,549,659 A | 8/1996 | Johansen et al. |
| 5,551,427 A | 9/1996 | Altman |
| 5,556,421 A | 9/1996 | Prutchi et al. |
| 5,562,717 A | 10/1996 | Tippey et al. |
| 5,571,143 A | 11/1996 | Hoegnelid et al. |
| 5,571,148 A | 11/1996 | Loeb et al. |
| 5,579,775 A | 12/1996 | Dempsey et al. |
| 5,586,556 A | 12/1996 | Spivey et al. |
| 5,591,217 A | 1/1997 | Barreras |
| 5,598,848 A | 2/1997 | Swanson et al. |
| 5,649,952 A | 7/1997 | Lam |
| 5,650,759 A | 7/1997 | Hittman et al. |
| 5,654,984 A | 8/1997 | Hershbarger et al. |
| 5,662,689 A | 9/1997 | Elsberry et al. |
| 5,669,391 A | 9/1997 | Williams |
| 5,674,259 A | 10/1997 | Gray |
| 5,676,153 A | 10/1997 | Smith et al. |
| 5,693,076 A | 12/1997 | Kaemmerer |
| 5,694,940 A | 12/1997 | Unger et al. |
| 5,694,952 A | 12/1997 | Lidman et al. |
| 5,697,958 A | 12/1997 | Paul et al. |
| 5,702,427 A | 12/1997 | Ecker et al. |
| 5,725,559 A | 3/1998 | Alt et al. |
| 5,728,154 A | 3/1998 | Crossett et al. |
| 5,730,143 A | 3/1998 | Schwarzberg |
| 5,735,880 A | 4/1998 | Prutchi et al. |
| 5,738,102 A | 4/1998 | Lemelson |
| 5,740,811 A | 4/1998 | Hedberg et al. |
| 5,741,314 A | 4/1998 | Daly et al. |
| 5,766,231 A | 6/1998 | Erickson et al. |
| 5,792,205 A | 8/1998 | Alt et al. |
| 5,810,735 A | 9/1998 | Halperin et al. |
| 5,814,076 A | 9/1998 | Brownlee |
| 5,814,087 A | 9/1998 | Renirie |
| 5,814,089 A | 9/1998 | Stokes et al. |
| 5,824,016 A | 10/1998 | Ekwall |
| 5,871,451 A | 2/1999 | Unger et al. |
| 5,876,353 A | 3/1999 | Riff |
| 5,876,425 A | 3/1999 | Gord et al. |
| 5,891,178 A | 4/1999 | Mann et al. |
| 5,899,928 A | 5/1999 | Sholder et al. |
| 5,935,079 A | 8/1999 | Swanson et al. |
| 5,954,761 A | 9/1999 | Machek et al. |
| 5,957,861 A | 9/1999 | Combs et al. |
| 5,984,861 A | 11/1999 | Crowley |
| 5,987,352 A | 11/1999 | Klein et al. |
| 5,995,876 A | 11/1999 | Kruse et al. |
| 5,999,857 A | 12/1999 | Weijand et al. |
| 6,002,969 A | 12/1999 | Machek et al. |
| 6,004,269 A | 12/1999 | Crowley et al. |
| 6,061,596 A | 5/2000 | Richmond et al. |
| 6,076,016 A | 6/2000 | Feierbach |
| 6,080,187 A | 6/2000 | Alt et al. |
| 6,093,146 A | 7/2000 | Filangeri |
| 6,096,065 A | 8/2000 | Crowley |
| 6,102,874 A | 8/2000 | Stone et al. |
| 6,112,116 A | 8/2000 | Fischell et al. |
| 6,115,628 A | 9/2000 | Stadler et al. |
| 6,115,630 A | 9/2000 | Stadler et al. |
| 6,115,636 A | 9/2000 | Ryan |
| 6,119,031 A | 9/2000 | Crowley |
| 6,125,290 A | 9/2000 | Miesel |
| 6,125,291 A | 9/2000 | Miesel et al. |
| 6,128,526 A | 10/2000 | Stadler et al. |
| 6,129,751 A | 10/2000 | Lucchesi et al. |
| 6,132,390 A | 10/2000 | Cookston et al. |
| 6,132,456 A | 10/2000 | Sommer et al. |
| 6,134,459 A | 10/2000 | Roberts et al. |
| 6,134,470 A | 10/2000 | Hartlaub |
| 6,139,510 A | 10/2000 | Palermo |
| 6,141,584 A | 10/2000 | Rockwell et al. |
| 6,141,588 A | 10/2000 | Cox et al. |
| 6,141,592 A | 10/2000 | Pauly |
| 6,144,866 A | 11/2000 | Miesel et al. |
| 6,148,230 A | 11/2000 | KenKnight |
| 6,152,882 A | 11/2000 | Prutchi |
| 6,163,723 A | 12/2000 | Roberts et al. |
| 6,164,284 A | 12/2000 | Schulman et al. |
| 6,167,310 A | 12/2000 | Grevious |
| 6,178,349 B1 | 1/2001 | Kieval |
| 6,178,356 B1 | 1/2001 | Chastain et al. |
| 6,185,443 B1 | 2/2001 | Crowley |
| 6,185,452 B1 | 2/2001 | Schulman et al. |
| 6,185,464 B1 | 2/2001 | Bonner et al. |
| 6,188,932 B1 | 2/2001 | Lindegren |
| 6,190,324 B1 | 2/2001 | Kieval et al. |
| 6,198,952 B1 | 3/2001 | Miesel |
| 6,201,993 B1 | 3/2001 | Kruse et al. |
| 6,208,894 B1 | 3/2001 | Schulman et al. |
| 6,208,900 B1 | 3/2001 | Ecker et al. |
| 6,223,081 B1 | 4/2001 | Kerver |
| 6,230,059 B1 | 5/2001 | Duffin |
| 6,236,882 B1 | 5/2001 | Lee et al. |
| 6,240,321 B1 | 5/2001 | Janke et al. |
| 6,243,608 B1 | 6/2001 | Pauly et al. |
| 6,248,080 B1 | 6/2001 | Miesel et al. |
| 6,263,245 B1 | 7/2001 | Snell |
| 6,265,100 B1 | 7/2001 | Saaski et al. |
| 6,266,554 B1 | 7/2001 | Hsu et al. |
| 6,266,564 B1 | 7/2001 | Hill et al. |
| 6,272,379 B1 | 8/2001 | Fischell et al. |
| 6,280,409 B1 | 8/2001 | Stone et al. |
| 6,289,229 B1 | 9/2001 | Crowley |
| 6,306,088 B1 | 10/2001 | Krausman et al. |
| 6,310,960 B1 | 10/2001 | Saaski et al. |
| 6,315,721 B2 | 11/2001 | Schulman et al. |
| 6,324,418 B1 | 11/2001 | Crowley et al. |
| 6,324,421 B1 | 11/2001 | Stadler et al. |
| RE37,463 E | 12/2001 | Altman |
| 6,343,227 B1 | 1/2002 | Crowley |
| 6,343,233 B1 | 1/2002 | Werner et al. |
| 6,347,245 B1 | 2/2002 | Lee et al. |
| 6,358,202 B1 | 3/2002 | Arent |
| 6,361,522 B1 | 3/2002 | Scheiner et al. |
| 6,363,282 B1 | 3/2002 | Nichols et al. |
| 6,364,831 B1 | 4/2002 | Crowley |
| 6,370,434 B1 | 4/2002 | Zhang et al. |
| 6,381,492 B1 | 4/2002 | Rockwell et al. |
| 6,381,493 B1 | 4/2002 | Stadler et al. |
| 6,381,494 B1 | 4/2002 | Gilkerson et al. |
| 6,383,209 B1 | 5/2002 | Crowley |
| 6,385,593 B2 | 5/2002 | Linberg |
| 6,386,882 B1 | 5/2002 | Linberg |
| 6,397,100 B2 | 5/2002 | Stadler et al. |
| 6,402,689 B1 | 6/2002 | Scarantino et al. |
| 6,405,073 B1 | 6/2002 | Crowley et al. |
| 6,405,083 B1 | 6/2002 | Rockwell et al. |
| 6,409,674 B1 | 6/2002 | Brockway et al. |
| 6,409,675 B1 | 6/2002 | Turcott |
| 6,412,490 B1 | 7/2002 | Lee |
| 6,418,346 B1 | 7/2002 | Nelson et al. |
| 6,423,056 B1 | 7/2002 | Ishikawa et al. |
| 6,424,866 B2 | 7/2002 | Mika et al. |
| 6,428,484 B1 | 8/2002 | Battmer et al. |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,442,433 B1 | 8/2002 | Linberg |
| 6,444,970 B1 | 9/2002 | Barbato |
| 6,445,953 B1 | 9/2002 | Bulkes et al. |
| 6,458,145 B1 | 10/2002 | Ravenscroft et al. |
| 6,459,928 B2 | 10/2002 | Mika et al. |
| 6,459,937 B1 | 10/2002 | Morgan et al. |
| 6,466,820 B1 | 10/2002 | Juran et al. |
| 6,468,263 B1 | 10/2002 | Fischell et al. |

(56) References Cited

U.S. PATENT DOCUMENTS

| | | |
|---|---|---|
| 6,470,215 B1 | 10/2002 | Kraus et al. |
| 6,471,645 B1 | 10/2002 | Warkentin et al. |
| 6,472,991 B1 | 10/2002 | Schulman et al. |
| 6,477,424 B1 | 11/2002 | Thompson et al. |
| 6,480,733 B1 | 11/2002 | Turcott |
| 6,482,154 B1 | 11/2002 | Haubrich et al. |
| 6,484,055 B1 | 11/2002 | Marcovecchio |
| 6,484,057 B2 | 11/2002 | Ideker et al. |
| 6,490,487 B1 | 12/2002 | Kraus et al. |
| 6,496,715 B1 | 12/2002 | Lee et al. |
| 6,498,951 B1 | 12/2002 | Larson et al. |
| 6,500,168 B1 | 12/2002 | Jellie |
| 6,501,983 B1 | 12/2002 | Natarajan et al. |
| 6,512,949 B1 | 1/2003 | Combs et al. |
| 6,512,959 B1 | 1/2003 | Gomperz et al. |
| 6,522,926 B1 | 2/2003 | Kieval et al. |
| 6,522,928 B2 | 2/2003 | Whitehurst et al. |
| 6,539,257 B1 | 3/2003 | KenKnight |
| 6,542,781 B1 | 4/2003 | Koblish et al. |
| 6,556,860 B1 | 4/2003 | Groenewegen |
| 6,558,321 B1 | 5/2003 | Burd et al. |
| 6,564,807 B1 | 5/2003 | Schulman et al. |
| 6,567,680 B2 | 5/2003 | Swetlik et al. |
| 6,571,120 B2 | 5/2003 | Hutten |
| 6,574,509 B1 | 6/2003 | Kraus et al. |
| 6,574,511 B2 | 6/2003 | Lee |
| 6,580,946 B2 | 6/2003 | Struble |
| 6,580,948 B2 | 6/2003 | Haupert et al. |
| 6,584,351 B1 | 6/2003 | Ekwall |
| 6,584,352 B2 | 6/2003 | Combs et al. |
| 6,589,187 B1 | 7/2003 | Dirnberger et al. |
| 6,592,518 B2 | 7/2003 | Denker et al. |
| 6,594,523 B1 | 7/2003 | Levine |
| 6,597,948 B1 | 7/2003 | Rockwell et al. |
| 6,597,952 B1 | 7/2003 | Mika et al. |
| 6,609,023 B1 | 8/2003 | Fischell et al. |
| 6,611,710 B2 | 8/2003 | Gomperz et al. |
| 6,615,075 B2 | 9/2003 | Mlynash et al. |
| 6,622,043 B1 | 9/2003 | Kraus et al. |
| 6,647,292 B1 | 11/2003 | Bardy et al. |
| 6,648,823 B2 | 11/2003 | Thompson |
| 6,649,078 B2 | 11/2003 | Yu |
| 6,654,638 B1 | 11/2003 | Sweeney |
| 6,658,285 B2 | 12/2003 | Potse et al. |
| 6,658,297 B2 | 12/2003 | Loeb |
| 6,658,301 B2 | 12/2003 | Loeb et al. |
| 6,659,959 B2 | 12/2003 | Brockway et al. |
| 6,669,631 B2 | 12/2003 | Norris et al. |
| 6,681,135 B1 | 1/2004 | Davis et al. |
| 6,684,100 B1 | 1/2004 | Sweeney et al. |
| 6,687,540 B2 | 2/2004 | Marcovecchio |
| 6,687,546 B2 | 2/2004 | Lebel et al. |
| 6,689,117 B2 | 2/2004 | Sweeney et al. |
| 6,690,959 B2 | 2/2004 | Thompson |
| 6,694,191 B2 | 2/2004 | Starkweather et al. |
| 6,695,885 B2 | 2/2004 | Schulman et al. |
| 6,697,672 B2 | 2/2004 | Andersson |
| 6,697,677 B2 | 2/2004 | Dahl et al. |
| 6,699,200 B2 | 3/2004 | Cao et al. |
| 6,702,857 B2 | 3/2004 | Brauker et al. |
| 6,704,602 B2 | 3/2004 | Berg et al. |
| 6,711,440 B2 | 3/2004 | Deal et al. |
| 6,716,238 B2 | 4/2004 | Elliott |
| 6,721,597 B1 | 4/2004 | Bardy et al. |
| 6,728,572 B2 | 4/2004 | Hsu et al. |
| 6,728,574 B2 | 4/2004 | Ujhelyi et al. |
| 6,728,576 B2 | 4/2004 | Thompson et al. |
| 6,731,976 B2 | 5/2004 | Penn et al. |
| 6,731,979 B2 | 5/2004 | MacDonald |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,738,670 B1 | 5/2004 | Almendinger et al. |
| 6,741,877 B1 | 5/2004 | Shults et al. |
| 6,741,886 B2 | 5/2004 | Yonce |
| 6,746,404 B2 | 6/2004 | Schwartz |
| 6,754,538 B2 | 6/2004 | Linberg |
| 6,760,620 B2 | 7/2004 | Sippens Groenewegen |
| 6,764,446 B2 | 7/2004 | Wolinsky et al. |
| 6,768,923 B2 | 7/2004 | Ding et al. |
| 6,783,499 B2 | 8/2004 | Schwartz |
| 6,785,576 B2 | 8/2004 | Verness |
| 6,786,860 B2 | 9/2004 | Maltan et al. |
| 6,792,314 B2 | 9/2004 | Byers et al. |
| 6,799,069 B2 | 9/2004 | Weiner et al. |
| 6,804,559 B1 | 10/2004 | Kraus et al. |
| 6,804,561 B2 | 10/2004 | Stover |
| 6,809,507 B2 | 10/2004 | Morgan et al. |
| 6,811,533 B2 | 11/2004 | Lebel et al. |
| 6,813,519 B2 | 11/2004 | Lebel et al. |
| 6,821,154 B1 | 11/2004 | Canfield et al. |
| 6,823,217 B2 | 11/2004 | Rutten et al. |
| 6,824,512 B2 | 11/2004 | Warkentin et al. |
| 6,829,508 B2 | 12/2004 | Schulman et al. |
| 6,839,596 B2 | 1/2005 | Nelson et al. |
| 6,848,052 B2 | 1/2005 | Hamid et al. |
| 6,850,801 B2 | 2/2005 | Kieval et al. |
| 6,856,835 B2 | 2/2005 | Bardy et al. |
| 6,862,465 B2 | 3/2005 | Shults et al. |
| 6,862,480 B2 | 3/2005 | Cohen et al. |
| 6,865,420 B1 | 3/2005 | Kroll |
| 6,869,404 B2 | 3/2005 | Schulhauser et al. |
| 6,871,099 B1 | 3/2005 | Whitehurst et al. |
| 6,878,112 B2 | 4/2005 | Linberg et al. |
| 6,879,695 B2 | 4/2005 | Maltan et al. |
| 6,879,855 B2 | 4/2005 | Schulman et al. |
| 6,882,875 B1 | 4/2005 | Crowley |
| 6,889,081 B2 | 5/2005 | Hsu |
| 6,893,395 B1 | 5/2005 | Kraus et al. |
| 6,895,279 B2 | 5/2005 | Loeb et al. |
| 6,895,281 B1 | 5/2005 | Amundson et al. |
| 6,896,651 B2 | 5/2005 | Gross et al. |
| 6,897,788 B2 | 5/2005 | Khair et al. |
| 6,901,294 B1 | 5/2005 | Whitehurst et al. |
| 6,901,296 B1 | 5/2005 | Whitehurst et al. |
| 6,907,285 B2 | 6/2005 | Denker et al. |
| 6,907,293 B2 | 6/2005 | Grill et al. |
| 6,912,420 B2 | 6/2005 | Scheiner et al. |
| 6,917,833 B2 | 7/2005 | Denker et al. |
| 6,925,328 B2 | 8/2005 | Foster et al. |
| 6,931,327 B2 | 8/2005 | Goode, Jr. et al. |
| 6,999,821 B2 | 2/2006 | Jenney et al. |
| 7,001,372 B2 | 2/2006 | Richter |
| 7,023,359 B2 | 4/2006 | Goetz et al. |
| 7,027,876 B2 | 4/2006 | Casavant et al. |
| 7,146,222 B2 | 12/2006 | Boling |
| 7,146,225 B2 | 12/2006 | Guenst et al. |
| 7,164,950 B2 | 1/2007 | Kroll et al. |
| 7,181,505 B2 | 2/2007 | Haller et al. |
| 7,187,971 B2 | 3/2007 | Sommer et al. |
| 7,200,437 B1 | 4/2007 | Nabutovsky et al. |
| 7,212,870 B1 | 5/2007 | Helland |
| 7,277,754 B2 | 10/2007 | McCabe et al. |
| 7,289,853 B1 | 10/2007 | Campbell et al. |
| 7,363,090 B2 | 4/2008 | Halperin et al. |
| 7,558,631 B2 | 7/2009 | Cowan et al. |
| 7,565,195 B1 | 7/2009 | Kroll et al. |
| 7,616,991 B2 | 11/2009 | Mann et al. |
| 7,630,767 B1 | 12/2009 | Poore et al. |
| 7,634,313 B1 | 12/2009 | Kroll et al. |
| 7,848,823 B2 | 12/2010 | Drasler et al. |
| 7,937,148 B2 | 5/2011 | Jacobson |
| 7,945,333 B2 | 5/2011 | Jacobson |
| 8,010,209 B2 | 8/2011 | Jacobson |
| 8,295,939 B2 | 10/2012 | Jacobson |
| 8,352,025 B2 | 1/2013 | Jacobson |
| 8,457,742 B2 | 6/2013 | Jacobson |
| 8,527,068 B2 | 9/2013 | Ostroff |
| 8,543,205 B2 | 9/2013 | Ostroff |
| 8,738,147 B2 * | 5/2014 | Hastings ............ A61N 1/0565 607/32 |
| 2001/0031999 A1 | 10/2001 | Carter et al. |
| 2002/0032467 A1 | 3/2002 | Shemer et al. |
| 2002/0077686 A1 | 6/2002 | Westlund et al. |

(56) References Cited

U.S. PATENT DOCUMENTS

| | | |
|---|---|---|
| 2002/0116028 A1 | 8/2002 | Greatbatch et al. |
| 2002/0147488 A1 | 10/2002 | Doan et al. |
| 2003/0141995 A1 | 7/2003 | Lin |
| 2003/0158584 A1 | 8/2003 | Cates et al. |
| 2003/0163184 A1 | 8/2003 | Scheiner et al. |
| 2003/0199941 A1 | 10/2003 | Nielsen et al. |
| 2004/0011366 A1 | 1/2004 | Schulman et al. |
| 2004/0059392 A1 | 3/2004 | Parramon et al. |
| 2004/0116939 A1 | 6/2004 | Goode |
| 2004/0133242 A1 | 7/2004 | Chapman et al. |
| 2004/0143262 A1 | 7/2004 | Visram et al. |
| 2004/0147973 A1 | 7/2004 | Hauser |
| 2004/0167587 A1 | 8/2004 | Thompson |
| 2004/0172116 A1 | 9/2004 | Seifert et al. |
| 2004/0193223 A1 | 9/2004 | Kramer et al. |
| 2004/0249417 A1 | 12/2004 | Ransbury et al. |
| 2004/0260349 A1 | 12/2004 | Stroebel |
| 2005/0038474 A1 | 2/2005 | Wool |
| 2005/0038491 A1 | 2/2005 | Haack |
| 2005/0043765 A1 | 2/2005 | Williams et al. |
| 2005/0075682 A1 | 4/2005 | Schulman et al. |
| 2005/0096702 A1 | 5/2005 | Denker et al. |
| 2005/0131478 A1 | 6/2005 | Kim et al. |
| 2005/0149138 A1 | 7/2005 | Min et al. |
| 2005/0165465 A1 | 7/2005 | Pianca et al. |
| 2005/0267555 A1 | 12/2005 | Marnfeldt et al. |
| 2005/0288722 A1 | 12/2005 | Eigler et al. |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0105613 A1 | 5/2006 | Carroll |
| 2006/0108335 A1 | 5/2006 | Zhao et al. |
| 2006/0121475 A1 | 6/2006 | Davids et al. |
| 2006/0135999 A1 | 6/2006 | Bodner et al. |
| 2006/0136004 A1 | 6/2006 | Cowan et al. |
| 2006/0161222 A1 | 7/2006 | Haubrich et al. |
| 2006/0241705 A1 | 10/2006 | Neumann et al. |
| 2006/0247750 A1 | 11/2006 | Seifert et al. |
| 2006/0282150 A1 | 12/2006 | Olson et al. |
| 2007/0016263 A1 | 1/2007 | Armstrong et al. |
| 2007/0043414 A1 | 2/2007 | Fifer et al. |
| 2007/0055184 A1 | 3/2007 | Echt et al. |
| 2007/0088396 A1 | 4/2007 | Jacobson |
| 2007/0088397 A1 | 4/2007 | Jacobson |
| 2007/0123923 A1 | 5/2007 | Lindstrom et al. |
| 2007/0142709 A1 | 6/2007 | Martone et al. |
| 2007/0179552 A1 | 8/2007 | Dennis et al. |
| 2007/0270675 A1 | 11/2007 | Kane et al. |
| 2007/0276004 A1 | 11/2007 | Hirsch et al. |
| 2007/0276444 A1 | 11/2007 | Gelbart et al. |
| 2007/0293904 A1 | 12/2007 | Gelbart et al. |
| 2008/0004535 A1 | 1/2008 | Smits |
| 2008/0021532 A1 | 1/2008 | Kveen et al. |
| 2008/0039738 A1 | 2/2008 | Dinsmoor et al. |
| 2008/0086168 A1 | 4/2008 | Cahill |
| 2008/0091255 A1 | 4/2008 | Caparso et al. |
| 2008/0119911 A1 | 5/2008 | Rosero |
| 2008/0243218 A1 | 10/2008 | Bottomley et al. |
| 2008/0269591 A1 | 10/2008 | Halperin et al. |
| 2009/0018599 A1 | 1/2009 | Hastings et al. |
| 2009/0082827 A1 | 3/2009 | Kveen et al. |
| 2009/0082828 A1 | 3/2009 | Ostroff |
| 2009/0149902 A1 | 6/2009 | Kumar et al. |
| 2009/0171408 A1 | 7/2009 | Solem |
| 2010/0069983 A1 | 3/2010 | Peacock, III et al. |
| 2010/0211149 A1 | 8/2010 | Morgan et al. |
| 2010/0249828 A1 | 9/2010 | Mavani et al. |
| 2010/0292541 A1 | 11/2010 | Hashiba et al. |
| 2010/0305653 A1 | 12/2010 | Lund et al. |
| 2010/0305656 A1 | 12/2010 | Imran et al. |
| 2010/0312332 A1 | 12/2010 | Forster et al. |
| 2011/0004117 A1 | 1/2011 | Neville et al. |
| 2011/0071586 A1 | 3/2011 | Jacobson |
| 2011/0077708 A1 | 3/2011 | Ostroff |
| 2011/0208260 A1 | 8/2011 | Jacobson |
| 2011/0282423 A1 | 11/2011 | Jacobson |
| 2012/0095539 A1 | 4/2012 | Khairkhahan et al. |
| 2012/0109236 A1 | 5/2012 | Jacobson et al. |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0197373 A1 | 8/2012 | Khairkhahan et al. |
| 2012/0245665 A1 | 9/2012 | Friedman et al. |
| 2013/0041422 A1 | 2/2013 | Jacobson |
| 2013/0103109 A1 | 4/2013 | Jacobson |
| 2013/0123875 A1 | 5/2013 | Varady et al. |
| 2013/0231710 A1 | 9/2013 | Jacobson |

FOREIGN PATENT DOCUMENTS

| | | |
|---|---|---|
| JP | 05-245215 | 9/1993 |
| JP | 06/507096 | 3/2006 |
| JP | 06/516449 | 7/2006 |
| JP | 2006-526483 A | 11/2006 |
| WO | WO93/12714 A1 | 7/1993 |
| WO | WO02/34333 A2 | 5/2002 |
| WO | WO2004/012811 | 2/2004 |
| WO | WO 2006/065394 A1 | 6/2006 |
| WO | WO 2007/047681 A2 | 4/2007 |
| WO | WO 2007/059386 A2 | 5/2007 |
| WO | WO 2008/058265 A2 | 5/2008 |
| WO | WO2010/088116 A1 | 8/2010 |

OTHER PUBLICATIONS

Beeby et al.; Micromachined silicon generator for harvesting power from vibrations; (Proceedings) PowerMEMS 2004; Kyoto, Japan; pp. 104-107; Nov. 28-30, 2004.

Bordacher et al.; Impact and prevention of far-field sensing in fallback mode switches; PACE; vol. 26 (pt. II); pp. 206-209; Jan. 2003.

Brandt et al.; Far-field QRS complex sensing: prevalence and timing with bipolar atrial leads; PACE; vol. 23; pp. 315-320; Mar. 2000.

Brown, Eric S.; The atomic battery; Technology Review: Published by MIT; 4 pgs.; Jun. 16, 2005.

Irnich et al.; Do we need pacemakers resistant to magnetic resonance imaging; Europace; vol. 7; pp. 353-365; Feb. 2005.

Irnich; Electronic security systems and active implantable medical devices; Journal of PACE; vol. 25; No. 8; pp. 1235-1258; Aug. 2002.

Luechinger et al.; Force and torque effects of a 1.5-tesla MRI scanner of cardiac pacemakers and ICDs; Journal of PACE; vol. 24; No. 2; pp. 199-205; Feb. 2001.

Luechinger et al.; In vivo heating of pacemaker leads during magnetic resonance imaging; European Heart Journal; vol. 26; pp. 376-383; Feb. 2005.

Lüchinger ; Safety aspects of cardiac pacemakers in magnetic resonance imaging; Dissertation submitted to the Swiss Federal Institute of Technology Zurich; 137 pages; (year of publication is sufficiently earlier than the effective U.S. filing date and any foreign priority date) 2002.

Nyenhuis et al.; MRI and Implanted Medical Devices: Basic Interactions with an emphasis on heating; vol. 5; No. 3; pp. 467-480; Sep. 2005.

Shellock et al.; Cardiac pacemaker: In vitro assessment at 1.5 T; Am Heart J; vol. 151; No. 2; pp. 436-443; Feb. 2006.

Pertijs et al.; U.S. Appl. No. 13/901,414 entitled "Temperature Sensor for a Leadless Cardiac Pacemaker," filed May 23, 2013.

Ostroff et al.; U.S. Appl. No. 13/910,896 entitled "Leadless Pacemaker with Multiple Electrodes," filed Jun. 5, 2013.

Ostroff, Alan; U.S. Appl. No. 13/915,560 entitled "MRI Compatible Leadless Cardiac Pacemaker," filed Jun. 11, 2013.

Carroll et al.; U.S. Appl. No. 13/956,946 entitled "Biostimulator Circuit with Flying Cell," filed Aug. 1, 2013.

\* cited by examiner

LEADLESS CARDIAC PACEMAKER WITH SECONDARY FIXATION CAPABILITY

CROSS REFERENCE TO RELATED APPLICATIONS

This application is a continuation of U.S. patent application Ser. No. 12/698,969, now U.S. Pat. No. 8,527,068, filed Feb. 2, 2010, which application claims the benefit under 35 U.S.C. 119 of U.S. Provisional Patent Application No. 61/149,176, filed Feb. 2, 2009, titled "Leadless Cardiac Pacemaker With Secondary Fixation Capability", and U.S. Provisional Patent Application No. 61/155,038, filed Feb. 24, 2009, titled "Leadless Cardiac Pacemaker With Secondary Fixation Capability". These applications are herein incorporated by reference in their entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

The present invention relates to leadless cardiac pacemakers, and more particularly, to features and methods by which they are affixed within the heart.

BACKGROUND OF THE INVENTION

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle". Even without persistent manipulation, subcutaneous pulse generators can exhibit erosion, extrusion, infection, and disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The male connector mates with a corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. This briefly described complex connection between connectors and leads provides multiple opportunities for malfunction.

Other problematic aspects of conventional pacemakers are enumerated in the related applications, many of which relate to the separately implanted pulse generator and the pacing leads. By way of another example, the pacing leads, in particular, can become a site of infection and morbidity. Many of the issues associated with conventional pacemakers are resolved by the development of a self-contained and self-sustainable pacemaker, or so-called leadless pacemaker, as described in the related applications cited above.

Self-contained or leadless pacemakers or other biostimulators are typically fixed to an intracardial implant site by an actively engaging mechanism such as a screw or helical member that screws into the myocardium. Examples of such leadless biostimulators are described in the following publications, the disclosures of which are incorporated by reference: (1) U.S. application Ser. No. 11/549,599, filed on Oct. 13, 2006, now U.S. Pat. No. 8,457,742, entitled "Leadless Cardiac Pacemaker System for Usage in Combination with an Implantable Cardioverter-Defibrillator"; (2) U.S. application Ser. No. 11/549,581 filed on Oct. 13, 2006, entitled "Leadless Cardiac Pacemaker", and published as US2007/0088396A1 on Apr. 19, 2007; (3) U.S. application Ser. No. 11/549,591, filed on Oct. 13, 2006, entitled "Leadless Cardiac Pacemaker System with Conductive Communication" and published as US2007/0088397A1 on Apr. 19, 2007; (4) U.S. application Ser. No. 11/549,596 filed on Oct. 13, 2006, now U.S. Pat. No. 8,352,025, entitled "Leadless Cardiac Pacemaker Triggered by Conductive Communication"; (5) U.S. application Ser. No. 11/549,603 filed on Oct. 13, 2006, now U.S. Pat. No. 7,937,148, entitled "Rate Responsive Leadless Cardiac Pacemaker"; (6) U.S. application Ser. No. 11/549,605 filed on Oct. 13, 2006, now U.S. Pat. No. 7,945,333, entitled "Programmer for Biostimulator System"; (7) U.S. application Ser. No. 11/549,574, filed on Oct. 13, 2006, now U.S. Pat. No. 8,010,209, entitled "Delivery System for Implantable Biostimulator"; and (8) International Application No. PCT/US2006/040564, filed on Oct. 13, 2006, entitled "Leadless Cardiac Pacemaker and System" and published as WO07047681A2 on Apr. 26, 2007.

The site of attachment of leadless biostimulators is physically reinforced by a foreign body response that results in the growth of fibrotic tissue that further secures the leadless biostimulator at the attachment site. A high degree of success of attachment by such an approach notwithstanding, the potential of detachment of the leadless biostimulator from the implant site would represent an immediately serious event, as for example, a pacemaker lost from the right ventricle can exit the heart via the pulmonic valve and lodge in the lung. Leadless or self-contained biostimulators would benefit from mechanisms and methods for "secondary fixation" of the device within the heart, or more generally, features that in the event of failure of the primary fixation to the implant site would prevent escape of the pacemaker into the circulation downstream from the heart.

SUMMARY OF THE INVENTION

The invention relates to a leadless cardiac pacemaker, a device more generally referred to as a leadless biostimulator (LBS), which includes a primary fixation element and a secondary fixation element. The invention also relates to methods of implanting a biostimulator with such a secondary fixation feature, and more generally to methods for retaining a leadless biostimulator in the heart in the event that the biostimulator is dislodged from its site of primary fixation.

With regard to embodiments of a leadless biostimulator with both primary and secondary fixation features, embodiments of the primary fixation element may be either active or passive; active elements typically requiring an active engagement of the element to a portion of the heart on the part of the user implanting the LBS and/or an active or at least minimally invasive engagement of heart structure, and the passive embodiments not so-requiring.

Embodiments of the secondary fixation element or assembly may also be characterized as active or passive. Exemplary embodiments of active forms of a secondary fixation assembly include an anchor and a tether, the tether connecting the LBS to the anchoring site, the anchoring being established by securely engaging or embedding within heart or vascular structure at the time of implantation. Various types of more passive forms of secondary fixation are also provided by the invention. Exemplary embodiments of passive forms of the secondary fixation element or assembly include features that engage or engage, snag, or entangle structural features within the heart and thereby prevent its escape downstream in the event that it becomes dislodged from the primary fixation site. Some embodiments of passive types of fixation include entangling elements connected to the LBS which become entangled in structural features within the heart chamber where the LBS is implanted. Other embodiments of passive types of fixation include heart structure-engaging elements that engage or snag heart structure that is located upstream from the site of primary fixation. Still other embodiments of passive types of fixation include expandable structures which, in their expanded configuration, have a minimal cross-sectional dimension that is greater than the diameter of the vascular exit pathway from the heart chamber in which the LBS is implanted.

Embodiments of a leadless biostimulator typically include a primary fixation element adapted to affix the biostimulator to a primary fixation site on a heart wall within a heart chamber; and a downstream vascular escape prevention assembly adapted to prevent an escape of the biostimulator in the event of it being dislodged from the implant site in a chamber of the heart. Other components of the leadless biostimulator include a power source adapted to be disposed within a human heart chamber, an electrode in electrical communication with the power source and adapted to be placed in contact with tissue within the heart chamber, a controller adapted to be disposed within the heart chamber and to control delivery of electrical energy from the power source to the electrode. Some embodiments of the leadless biostimulator include a housing within which the power source, the electrode, and the controller are disposed. Some embodiments of the biostimulator may be adapted for implantation in the right ventricle or the left ventricle of the heart; in other embodiments, the biostimulator may be implanted in the left or right atrium of the heart.

Some embodiments of a leadless biostimulator have a downstream vascular escape prevention assembly that includes one or more entangling elements adapted to entangle within heart structure at one or more secondary fixation sites within the chamber of the heart. In some of these embodiments, the one or more entangling elements may include any of tines, hooks, or chains. Typical embodiments of entangling elements are adapted to extend radially outward beyond the diameter of the biostimulator, particularly after the biostimulator is implanted. Some of the entangling element embodiments are at least 5 mm in length. Some of the entangling element embodiments extend outward from the biostimulator at a proximal-facing angle that ranges from about 10 degrees to about 90 degrees from the axis of the biostimulator. Some of the entangling element embodiments such as tines are configured as any of straight tines, curvilinear tines, or convoluted tines.

Some of the entangling element embodiments are adapted to be rotatable with respect to the biostimulator, as for example, they may be mounted on a rotatable collar encircling the main axis of the biostimulator. Some of the entangling element embodiments are configured such that they are distally-collapsible around the periphery of the biostimulator. When collapsed, typical embodiments of collapsible entangling elements are configured to be substantially contained within a maximal diameter of the biostimulator, or add a minimal increment to such maximal diameter.

As noted above, some embodiments of passive secondary fixation element engage heart structure upstream from the site of primary fixation. Thus, a leadless biostimulator that includes this form of secondary fixation, in addition to the power source, electrode, controller, and primary fixation element, as summarized above, includes a downstream vascular escape prevention assembly adapted to prevent an escape of the biostimulator in the event of it being dislodged from the primary fixation site, such assembly including a heart structure engaging element adapted to passively engage or snag a heart structure as a secondary fixation site within the heart.

Embodiments of this particular downstream vascular escape prevention assembly include a tail attached to the distal portion of the biostimulator. Such a tail may include a metallic core, and such core may further include a multifilar wrapping around the core. The tail may further include a polymeric coating, such as polyurethane or silicone. The tail may further include surface features or agents that discourage the attachment and colonization of the surface of the tail by cells, such as blood borne cells or cardiac tissue cells. Various embodiments of the tail may also include an atraumatic tip configured to prevent damage to cardiac tissue, and the tail may also include a feature that is adapted to enhance capturabilty of the LBS by a retrieval device.

Still other embodiments of a leadless biostimulator that include a passive secondary fixation element may be summarized as a leadless biostimulator that includes a power source adapted to be disposed within a chamber of a human heart, an electrode in electrical communication with the power source and adapted to be placed in contact with tissue within the heart chamber, a controller adapted to be disposed within the heart chamber and to control delivery of electrical energy from the power source to the electrode, a primary fixation element adapted to affix the biostimulator to a primary fixation site on a heart wall within the heart chamber; and a downstream vascular escape prevention assembly adapted to prevent an escape of the biostimulator in the event of it being dislodged from the primary fixation site, the downstream vascular escape prevention assembly comprising an expandable structure. The expandable structure has a constrained or compressed configuration appropriate for deployment and an unconstrained default or radially expanded configuration. This radially-expanded configuration, in comparison to the compressed configuration, has a minimal cross-sectional linear dimension greater than a downstream vascular exit from the heart chamber. Some embodiments of the expandable structure formed at least in part from a shape memory material, such as Nitinol, whose properties confer on the structure an ability to return to a default or unconstrained configuration, after being forced or constrained into an alternative configuration.

The leadless biostimulator, as just summarized, may further include a coupling mechanism that couples the expandable structure to a proximal portion of the biostimulator. In some particular embodiments, the coupling mechanism is adapted to provide freedom of movement between the expandable structure and the biostimulator, as for example the coupling mechanism may include a swivel, a tether, a universal joint, a combination of any of the preceding mechanisms, or any conventional mechanism that provides a freedom of movement between two coupled structures.

Embodiments of the expandable structure of the leadless biostimulator, as summarized above, have a central longitudinal axis and may include struts disposed parallel to that longitudinal axis, which collectively form the expandable structure. These struts typically have a native bowed configuration, and they may further be adapted to be constrainable into a linear configuration without compromising their ability to return to a native configuration. In some embodiments, the bowed configuration is longitudinally symmetrical. In other embodiments, the bowed configuration is longitudinally asymmetrical, such that, for example, the asymmetrical bowed configuration is distributed such that a greater radial diameter is proximally-skewed.

Some embodiments of a the leadless biostimulator have a downstream vascular escape prevention assembly that includes a tether and an anchor, the tether connecting the assembly and the anchor to each other, and the anchor adapted to anchor at a secondary attachment site. In these embodiments, the anchor may include any of a screw, a hook, a clip, a stent, a cage, or a barb to attach the biostimulator to the secondary attachment site. The attachment site to which the anchor plus tether embodiments of secondary fixation to which the anchor is adapted to affix may be any of an intracardiac site, an intravascular site, or an extravascular site. In some embodiments, the intracardiac site is a septal wall of the heart. In other embodiments, the intravascular site is located within a vessel through which the biostimulator was delivered to the heart. Such vessels may include, for example, any of the femoral vein or the inferior vena cava. In some of these embodiments, the tether of the biostimulator is formed from two segments secured together with a clip. In other embodiments, an extravascular site may include the external periphery of a vessel through which the biostimulator was delivered to the heart. In these embodiments, the tether is typically adapted to be threaded through the vessel wall and to be attached to an anchor, the anchor including, by way of example, any of a partial cylinder, a plate, or a ball. In some anchor-plus-tether embodiments, the connection between the anchor and the tether, or between the tether and the biostimulator may include intervening or connective elements.

In some embodiments of a leadless biostimulator, the anchor may include one or more electrodes for biostimulation, wherein the tether itself is electrically conductive. In some embodiments, the tether may include any of single strand wire, multistranded wire, monofilament suture thread, or multistrand suture thread. In some embodiments, a tether or any of the anchor itself, or entangling elements may include any of a biodegradable material or an antithrombogenic agent.

Some embodiments of a leadless biostimulator may include one or more soluble coverings configured to encapsulate any of the primary fixation element or the secondary fixation element. Some embodiments of the soluble covering may include biocompatible materials, such as, merely by way of example, a polymer (such as polyvinylpyrrolidone), a protective sugar (such as mannitol), or a protective salt. In typical embodiments that make use of a soluble covering that is useful in deployment of the device, the soluble covering secures the secondary element in a collapsed configuration.

As mentioned above, embodiments of the invention also include a method for retaining a leadless intracardiac biostimulator in the heart in the event of dislodgement from a primary fixation site. In some embodiments, the method including the step of entangling an element of the biostimulator within the heart structure at a site within a heart chamber, such entanglement being sufficient to retain the biostimulator within the cardiac chamber. Embodiments of this method may include entangling the biostimulator or an element of the biostimulator within heart structures such as trabeculae in either the left or right ventricle. In another aspect, some embodiments of the invention include preventing escape of the biostimulator into a downstream vascular site, such as the aorta, if preventing escape from the left ventricle, or the pulmonary artery, if preventing escape from the right ventricle.

Some embodiments of the method for retaining a leadless biostimulator in the heart in the event of dislodgement from the primary fixation site include engaging a heart structure-engaging element of the biostimulator within or at a heart structure at as a secondary fixation site within the heart, such engagement being sufficient to retain the biostimulator within the heart chamber. In these embodiments, the engaging step may include positioning a tail connected to a proximal portion of the leadless biostimulator into a second heart chamber. The engaging step may also include restricting the range of movement of the biostimulator in the heart chamber such that the longitudinal axis of the biostimulator cannot be aligned in a direction of downstream blood flow within the heart chamber.

In various embodiment of the method that utilize a proximal tail to engage a heart structure, the first heart chamber is a ventricle and the heart structure includes an atrium. For example, the ventricle can be the right ventricle, in which case the heart structure is the right atrium, and such heart structure may also include the tricuspid valve. As another example, the ventricle can be the left ventricle, in which case the heart structure is the left atrium and/or a semilunar valve. In these embodiments, typically, the engaged heart structure is a heart chamber through which the biostimulator passed prior to being implanted at the primary fixation site in the first heart chamber.

Some embodiments of a method for retaining a leadless biostimulator in a heart chamber in the event of dislodgement from a primary fixation site include expanding an expandable structure to a dimension larger than a diameter of a downstream vascular exit from the heart chamber. In various of these embodiments, the heart chamber is a right ventricle and the downstream vascular structure is a pulmonic valve. Some of these embodiments include coupling an embodiment of an expandable structure to the proximal portion of the leadless biostimulator.

These methods may include, prior to the expanding step, delivering the leadless biostimulator to the heart chamber with the expandable structure in a compressed configuration. After delivery of the LBS to the heart chamber, the method typically includes expanding the expandable structure, and such expanding typically includes bowing struts of the expandable structure from a linear configuration to a bowed configuration.

In some embodiments of the method, expanding the expandable structure comprises expanding the structure in the same heart chamber in which the site of primary fixation is located. The method may further include preventing escape of the biostimulator into a downstream vascular site. Some particular embodiments include preventing escape into the pulmonary artery.

Some embodiments of a method for retaining a leadless intracardiac biostimulator in a heart in the event of dislodgement from a primary fixation site include anchoring the biostimulator with a tether to a secondary anchoring site, the tether being of appropriate length (e.g., sufficiently short) to prevent substantial movement into a downstream vascular from a biostimulator implant site in a heart chamber. In some aspects, anchoring the biostimulator with a tether includes anchoring with a tether of appropriate length to retain the biostimulator within the heart chamber.

In some embodiments, anchoring the biostimulator with a tether includes attaching the tether to an anchor at the secondary fixation site. Such attaching may include attaching the tether to the secondary fixation site with any of a screw, a hook, a clip, a stent, a cage, or a barb.

In various aspects, anchoring the biostimulator to a secondary anchoring site can include anchoring to either an intracardiac site or an extracardial site. In some embodiments, anchoring to an extracardial site includes anchoring to a site on a vessel through which the biostimulator was delivered to the heart. Also, in these embodiments, the anchoring site may be on either an internal or an exterior surface of the vessel.

Some embodiments of a method for retaining a leadless intracardiac biostimulator in a heart in the event of dislodgement from a primary fixation site that include anchoring the biostimulator with a tether to a secondary anchoring site include combining two tethers to form a single tether. Such a method of forming a single combined tether from two original tethers can include inserting a biostimulator attached to a first tether into an entry site in the vasculature, advancing the biostimulator to an intracardial implant site, and implanting the biostimulator at that site, inserting an anchor attached to a second tether into the entry site in the vasculature, advancing the anchor to a secondary anchoring site, and implanting the anchor at that site, and engaging the tether of the biostimulator and the tether of the anchor within a slidable clip at the vascular entry site to form a combined tether. Embodiments of this method may further include adjusting the length of the combined tether by slidably advancing the clip within the vasculature toward secondary anchoring site, and securing the first tether and the second tether at the clip so that no further sliding can occur. More specifically, adjusting the length of the combined tether may include adjusting the length such that there is an appropriate level of slack between the anchoring site and the biostimulator.

In another aspect, rescuing a leadless biostimulator dislodged from its primary fixation site may include a user grasping any portion of a secondary fixation element with a tool, and withdrawing the dislodged biostimulator from the heart chamber in which it was implanted.

In one embodiment, a leadless biostimulator is provided comprising a housing sized and configured to be disposed within a heart chamber of a human, a primary fixation element configured to affix the biostimulator to a heart wall within the heart chamber, and a passive secondary fixation element configured to prevent an escape of the biostimulator from the heart chamber when the primary fixation element is not affixed to the heart wall, the passive secondary fixation element comprising a tail portion sized and configured to extend from the heart chamber into a second heart chamber without being attached to the human.

In some embodiments, the passive secondary fixation element is sized and configured to be fully disposed within the heart.

In one embodiment, the heart chamber is a right ventricle of the heart and the second heart chamber is a right atrium of the heart, wherein the passive secondary fixation element is sized and configured to extend from the right ventricle through a tricuspid valve into the right atrium.

In some embodiments, the passive secondary fixation element is configured to be grasped by a retrieval tool.

In some embodiments, the passive secondary fixation element is of sufficient stiffness to prevent a dislodged leadless biostimulator from turning or reorienting itself within the heart chamber. The passive secondary fixation element can comprise silicone, polyurethane or any suitable polymer, a flexible metallic core, and/or multifilar windings around the flexible metallic core, for example.

In some embodiments, the passive secondary fixation element comprises an atraumatic tip.

In another embodiment, a leadless biostimulator comprises a housing sized and configured to be disposed within a heart chamber of a human, a primary fixation element configured to affix the biostimulator to a heart wall within the heart chamber, and a passive secondary fixation element configured to prevent an escape of the biostimulator from the heart chamber when the primary fixation element is not affixed to the heart wall, the passive secondary fixation element comprising an expandable structure having a strut, wherein first and second ends of the strut are attached to the housing.

In some embodiments, the passive secondary fixation element is sized and configured to be fully disposed within the heart chamber. The heart chamber, for example, can be the same heart chamber in which the biostimulator is disposed.

In some embodiments, the expandable structure allows deformation into a constrained configuration and a high-fidelity return to a native expanded configuration upon being released from constraint.

In other embodiments, the expandable structure has a minimal cross-sectional linear dimension greater than a diameter of a downstream vascular exit from the heart chamber.

In one embodiment, the strut is disposed parallel to a longitudinal axis of the expandable structure.

In some embodiments, the strut has a native bowed configuration. The bowed configuration can be longitudinally symmetrical or asymmetrical, for example. The asymmetrical bowed configuration can be distributed such that a greater radial diameter is proximally-skewed.

In some embodiments, the strut is configured to be constrainable into a linear configuration without compromising its ability to return to a native configuration.

In some embodiments, the passive secondary fixation device can further comprise a coupling mechanism that couples the expandable structure to the housing. The coupling mechanism can be configured to provide freedom of movement between the expandable structure and the housing. In some embodiments, the coupling mechanism comprises a swivel or a tether.

In one embodiment, the expandable structure comprises a shape memory material, such as Nitinol.

A method of retaining a leadless biostimulator within a human heart of a patient is provided, comprising delivering the leadless biostimulator to a heart chamber, affixing a primary fixation element of the leadless biostimulator to a heart wall of the heart chamber, and extending a passive secondary fixation element of the leadless biostimulator from the heart chamber to a second heart chamber without attaching the secondary fixation element to the patient.

In some embodiments, the passive secondary fixation element can be sized and configured to be fully disposed within the human heart.

In one embodiment, the heart chamber is a right ventricle of the heart and the second heart chamber is a right atrium of the heart. The passive secondary fixation element can be extended from the right ventricle to the right atrium through a tricuspid valve.

In one embodiment, the passive secondary fixation element is of sufficient stiffness to prevent a dislodged leadless biostimulator from turning or reorienting itself within the heart chamber.

Another method of retaining a leadless biostimulator within a human heart of a patient is provided, comprising delivering the leadless biostimulator to a heart chamber, affixing a primary fixation element of the leadless biostimulator to a heart wall of the heart chamber, and expanding a passive secondary fixation element of the leadless biostimulator within the heart chamber, the passive secondary fixation element comprising a strut wherein first and second ends of the strut are attached to the leadless biostimulator.

In some embodiments, the passive secondary fixation element is expanded to a dimension larger than a diameter of a downstream vascular structure from the heart chamber.

In one embodiment, the heart chamber is a right ventricle and the downstream vascular structure is a pulmonic valve.

In some embodiments, the delivery step further comprises delivering the leadless biostimulator to the heart chamber with the passive secondary fixation element in a compressed configuration.

In one embodiment, expanding the passive secondary fixation element comprises bowing the strut from a linear configuration to a bowed configuration.

Embodiments of the invention may further include fixation elements that are redundant, ancillary, or supportive of primary fixation, by, for example, minimizing movement of the biostimulator at the implant site. Such movement may include, for example, undesirable pitch, or yaw, or roll. Some of the embodiments may include rigid elements that are attached or connected to a primary fixation element on one end, and seated into or against heart structure on the other end. Some of these embodiments, which mainly serve in a primary fixation capacity, may further provide a secondary fixation.

BRIEF DESCRIPTION OF THE DRAWINGS

FIG. 1A shows the leadless biostimulator implanted at a primary fixation site in the right ventricle, with the proximal tail extending through the tricuspid valve and into the right atrium.

FIG. 1B shows the leadless biostimulator embodiment in a situation where it has unfortunately been dislodged from the primary fixation site, but is being retained within the right ventricle because it is prevented from becoming oriented toward the pulmonary valve by its proximal tail.

FIG. 2A shows the leadless biostimulator being delivered to the right ventricle within a delivery device with the struts of the expandable structure in a compressed linear configuration within the confines of the delivery device.

FIG. 2B shows the leadless biostimulator implanted at a primary fixation site in the right ventricle with the proximally-connected expandable structure in an expanded configuration.

FIG. 2C shows the leadless biostimulator as implanted with the right ventricle in a contracted state, the ventricle walls compressing the compliant expandable structure.

FIG. 3A shows a coupling mechanism that includes a swivel.

FIG. 3B shows a coupling mechanism that includes a short flexible tether.

DETAILED DESCRIPTION OF THE INVENTION

Figure 1A:
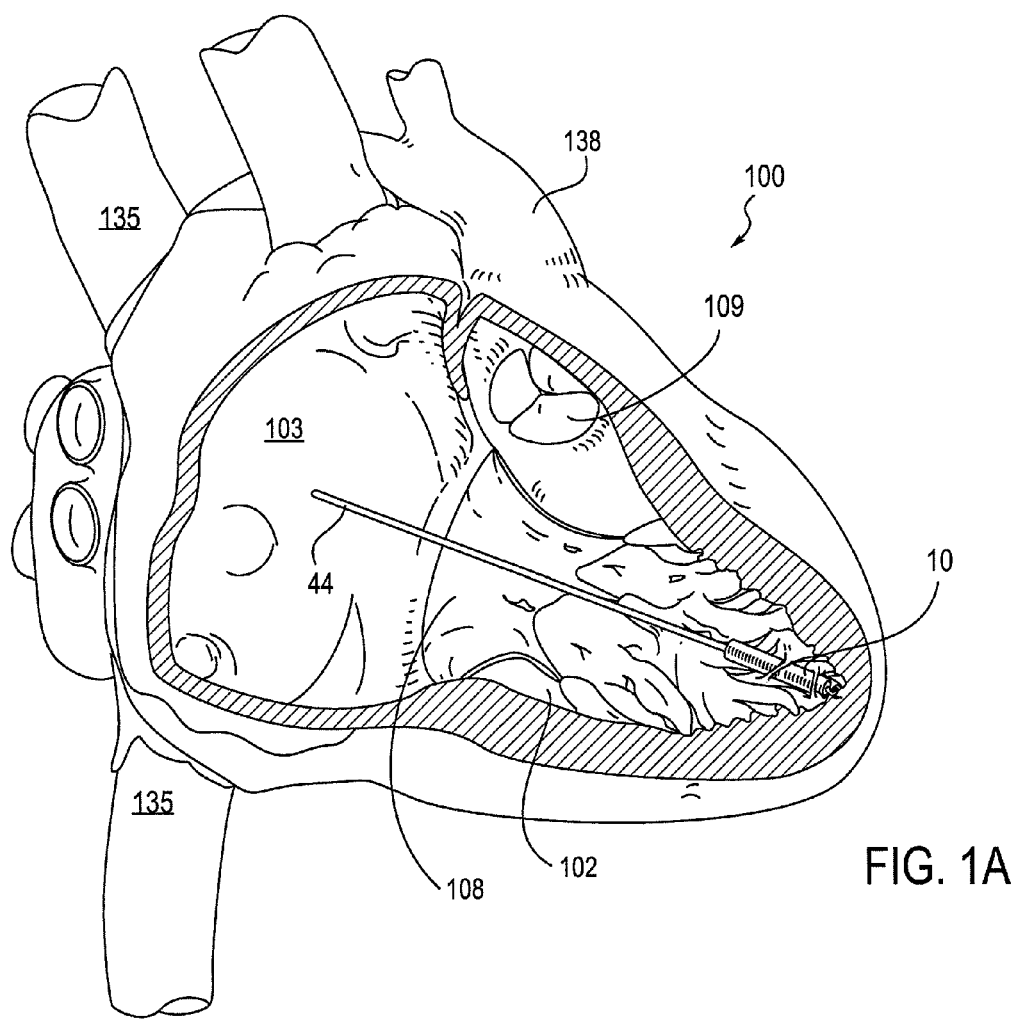
FIGS. 1A and 1B show an embodiment of a leadless biostimulator that has a secondary fixation element in the form of a tail portion that is sized to extend through the tricuspid valve when the biostimulator is placed in the right ventricle.

Leadless biostimulators (LBS's), also known as leadless cardiac pacemakers, for all their advantageous features over conventional pacemakers, could include as part of their profile a risk of loss into the downstream vasculature in the event of dislodgment from their site of primary fixation, were it not for the solution provided by embodiments of this invention. This invention provides various downstream vascular escape prevention methods and assemblies employing, e.g., "secondary fixation" in order to distinguish this form of attachment or fixation from "primary fixation". In this context, primary fixation generally refers to an attachment or fixation of a cardiac pacemaker to an intracardial implant site (or primary fixation site) such that at least one of the electrodes of the biostimulator stably remains in intimate contact with that site on the myocardium. In contrast, secondary fixation generally refers to an element or assembly that retains within the heart chamber a biostimulator that has become loose from its implant site, or prevents the biostimulator from moving any substantial distance into the vasculature downstream from the chamber in which it was implanted, when it has become dislodged.

Retention within the heart chamber thus involves the engagement of one or more secondary fixation elements, at one or more secondary fixation sites. The nature and location of secondary fixation sites may vary in accordance with the nature of the secondary fixation element or the downstream vascular prevention assembly embodiments. Some secondary fixation embodiments include elements that entangle themselves passively within or amongst structural features within the heart chamber, and thus these secondary sites are located within the heart chamber where the device is implanted. These intracardial entangling fixations may be temporary or transient, as the engagement of an entangling element with structure may include sliding or twisting, as examples of transient engagement. In some embodiments or instances, the secondary fixation brought about by an entangling element may effectively become as secure as a typical primary fixation site, either by the effectiveness of entanglement, or by fibrotic process of heart tissue that engages the entangling element. Other embodiments of secondary fixation assemblies, as described herein, may include assemblies comprising an anchor and a tether, the tether connecting the leadless biostimulator to the anchoring site. The anchoring site for these embodiments may be considered the secondary fixation site, and such sites may be intracardial or extracardial. The tether of these embodiments may be composed of any suitable material or mixture of materials, such as, by way of example, single-stranded wire, multi-stranded wire, monofilament suture thread, or multi-stranded suture thread.

Some tether embodiments, as well as other components of secondary fixation elements, may also include an anti-thrombogenic agent to discourage them from becoming a clot-forming nucleus. In some embodiments of the LBS and associated methods of use, the acute phase following implantation is of particular significance in that during that time, the initial period of days or weeks following implantation, the primary fixation becomes more secure, as for example, as a result of the growth of fibrotic tissue envelopes the implant site. Accordingly during that time, the secondary fixation is of particular importance because of the relative vulnerability of the primary fixation. Further, accordingly, in some embodiments it may be appropriate for the tether to include biodegradable materials that degrade over time, after the acute and vulnerable phase has passed. By a similar rationale, it may be appropriate, in some embodiments, for entangling elements or secondary anchors include biodegradable materials.

Secondary fixation embodiments may vary with regard to the extent to which they re-enforce, assist, support, provide redundancy, or protect the primary fixation method or element. Some embodiments of secondary fixation may serve in one or more of these recited primary fixation-related capacities, either minimally or significantly. Other embodiments for secondary fixation elements or assemblies may provide no substantial contribution to the primary fixation function, and function entirely in their secondary fixation capacity when called upon in the event of failure of the primary fixation.

The U.S. patent publications listed in the background above describe and depict two basic types of primary fixation elements. One embodiment of a primary fixation element is a helix (e.g., FIG. 1A of US 2007/0088418) that may be screwed directly into the myocardium to form a very stable and secure fixation. The screwable helix approach to primary fixation may be considered "active" in that it entails a screwing action to seat it, and it is at least to some extent invasive of the myocardium. A second embodiment of a primary fixation element described therein includes a small set of tines (e.g., FIG. 1B of US 2007/0088418) that may be used alone or in combination with a screwable helix, and which are designed particularly to establish lateral stability on the myocardial surface. The primary fixating tines may be considered relatively "passive", in comparison to the actively engaging screwable helix, as the engagement of the tines to the surface does not involve a screwing action, and the engagement is minimally invasive of the surface of the myocardium. Primary fixating tines typically do not extend or do not substantially extend beyond the diameter profile of the biostimulator, typically being less than 5 mm in length. Further, depending on the embodiment and the nature of the engagement of the primary fixating site, the tines may be directed at an angle that varies between proximal and distal. The fixation provided by these tines may serve as a stand-alone fixation element, but may also be used in conjunction with a helix, in which case they may be understood to be a redundant, back-up, or supportive form of primary fixation. Both types of primary fixation elements are subject to fibrotic overgrowth, as mentioned in the background, which further supports the fixation of the LBS at the attachment site.

The secondary fixation elements described herein perform a fail-safe function by, after failure of primary fixation, preventing loss of a dislodged LBS from a ventricle in which it is implanted, and they may further, in some embodiments, support stability of the LBS at the implant site. For example, if an LBS implanted in the right ventricle were to dislodge and exit the ventricle, it would leave through the pulmonic valve and lodge in the lungs. If an LBS implanted in the left ventricle were to exit the ventricle, it would enter the aorta and move into the general circulation, or the brain. A function of secondary fixation is to prevent occurrence of these catastrophic events should primary fixation fail. Some embodiments of the secondary fixation elements effectively retain a dislodged LBS within the ventricle, and other embodiments may allow exit from the ventricle for a very short distance but stop any substantial downstream movement. Dislodgment or detachment of an LBS from its implant site, even with loss from the ventricle and adverse downstream consequences being prevented, is nevertheless a serious medical emergency, and the loosed LBS needs to be retrieved. Thus, another benefit and function of the secondary fixation element is that it may contribute to the feasibility of a retrieval procedure, by providing an element easily graspable by a retrieval tool.

As with primary fixation elements, secondary fixation elements may be active (or actively-applied) or passive (or passively-engaging). Active secondary fixation elements include a tether that connects the LBS to an anchor at a secondary site, the anchor being a secure attachment made by active engagement of a portion of the heart or engagement at an extracardial site. Passive secondary fixation embodiments include elements that hook, snag, or otherwise entangle within intrachamber structural features of the heart, but they are substantially non-invasive of heart structure, nor are they actively seated during implantation of the LBS. Anatomical heart structure in the chamber in which the elements entangle includes connective tissue structures generally referred to as trabeculae carneae that are prominent in ventricles, and may also include ridges in the myocardium, and may also include tissue with a mix of fibrous and muscular tissue. Trabeculae carneae may be referred to simply as trabeculae in the cardiac context; the structures are attached to the chamber wall and vary in form, appearing as ridges, flaps, and cords.

Embodiments of passive secondary fixation elements or entangling elements are typically closely associated with the body of the LBS, i.e., they are integral with the body of the LBS, directly attached to it, or mounted on a rotatable collar encircling the LBS. A typical embodiment of an entangling element is a set of one or more tines projecting outwardly from the body of the LBS, as described and depicted in detail below. In some embodiments, tines may include features that further provide engaging or particularly entangleable features, such as hooks, typically atraumatic hooks, or linked elements, such as for example, serial structures threaded together, or linked as in a chain. Tines may assume various forms; they may be straight or curved, they may project at various angles from the leadless biostimulator, and they may have a collapsible bias. Such collapsibility is advantageous for several reasons. In one aspect collapsibility reflects a flexible and compliant quality of the tines which is compatible with them being a structure that does not interfere with primary fixation. Further, the collapsibility has a bias that is typically proximally directed; this bias is consistent with the configuration of the landscape of the heart chamber that surrounds the primary attachment site. Collapsibility also provides for a structure that folds easily and closely around the body of the leadless biostimulator, which is a property advantageous for being accommodated by a delivery device, and further is compatible with being enclosed within a soluble capsule for deployment, and expanding outward to post-deployment configuration after dissolution of the soluble capsule. Typically, embodiments of tines project outwardly beyond the diameter of the leadless biostimulator to which they are attached, and typically, such tines are about 5 mm in length or longer.

Entangling elements may be attached to the LBS housing at any point along the body from proximal end to distal end, although they are generally not located at the distal-most point, because that locale is typically the location of a primary fixation element. The rotatable collar may be understood as a mount upon which tines may rotate around the main axis of the LBS body, or, from the complementary perspective, as a collar within which the LBS body may rotate. Rotation of the LBS body within the collar allows the body to turn as a screw, a movement that embeds a primary fixating helix into the myocardium while allowing the tines to come to rest as they encounter obstructing trabeculae in which they entangle.

In another embodiment of secondary fixation, the secondary fixation element, a downstream vascular escape prevention assembly that is adapted to prevent an escape of the biostimulator in the event of it being dislodged from the primary fixation site, can be a passive heart structure-engaging element. Such structure may be within the same chamber as the primary fixation site, or it may be located elsewhere within the heart. As an example, a passive heart engaging element may engage or be engaged by a valve or a chamber that is upstream from the site of primary fixation. For example, an LBS implanted in the right ventricle may be engaged within the tricuspid valve and the right atrium.

Figure 1B:
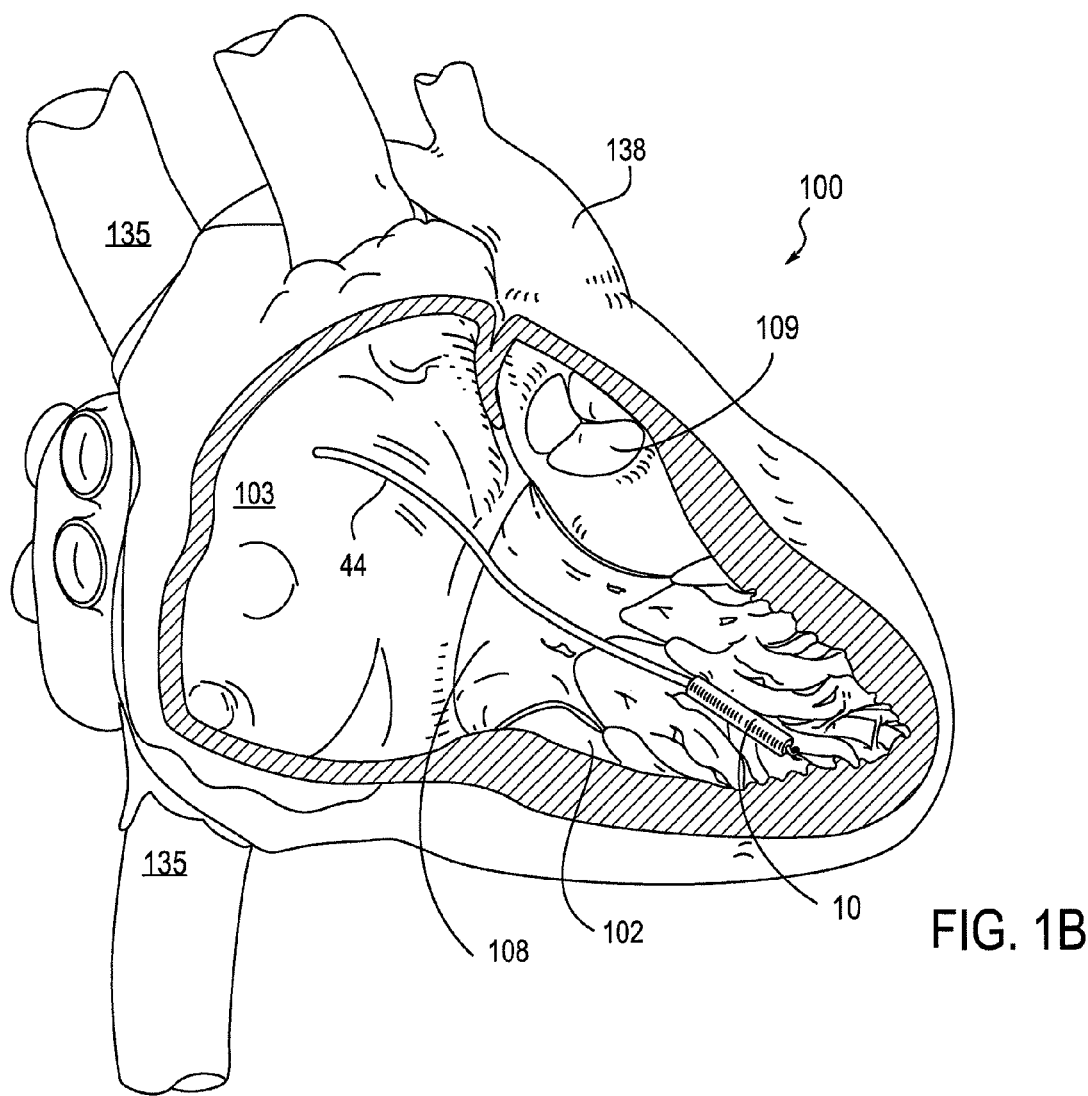

FIGS. 1A and 1B show an embodiment of a leadless biostimulator that has a secondary fixation element in the form of a tail portion that is sized to extend through the tricuspid valve when the biostimulator is placed in the right ventricle. FIG. 1A shows an embodiment of a leadless biostimulator 10 implanted in the right ventricle 102 of a heart 100, the LBS having a tail 44 extending from its proximal end that extends proximally through the tricuspid valve 108 and into the right atrium 103. As shown in FIGS. 1A-1B, the tail 44 is not affixed or attached to patient. As also shown in FIG. 1B, in the rare and unfortunate event of dislodgement of the LBS from its primary fixation site, the wire tail 44 is of sufficient stiffness that it prevents the loosed LBS from turning or reorienting itself within the heart chamber to the extent that it can turn and be aligned to enter the semilunar valve 109. By not being able to pass through the semilunar valve 109 and enter the pulmonary artery 138, the LBS necessarily remains within the right ventricle. The distal end of the tail remains projecting distally into the right atrium, where it can be grasped by a retrieval tool and retrieved. The tail portion 44 may include features that discourage attachment and colonization of its surface by cells of either blood or cardiac origin. Exemplary embodiments of the tail may include silicone or polyurethane or any suitable polymer, and may include a flexible metallic core. Stiffness can be added to a metallic core by the inclusion of multifilar windings around the core. In some embodiments, the tail 44 has an atraumatic tip adapted such that its contact with heart structure is benign, causing no irritation or injury. The tail 44 may additionally be adapted or configured to facilitate easy capture by a retrieval device.

Figure 2A:
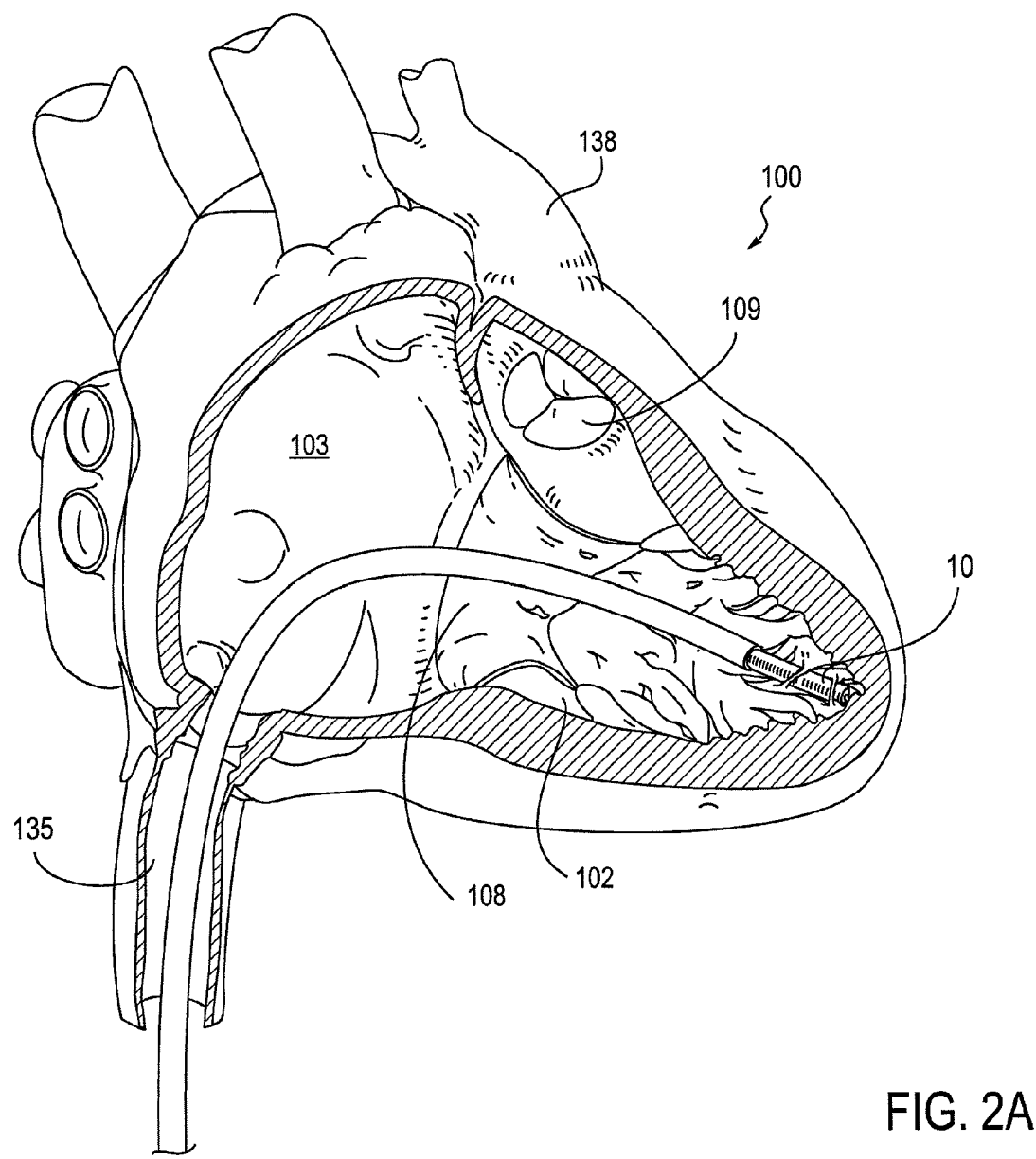
FIGS. 2A-2C show an embodiment of a leadless biostimulator with a proximally-connected expandable structure.
Figure 2B:
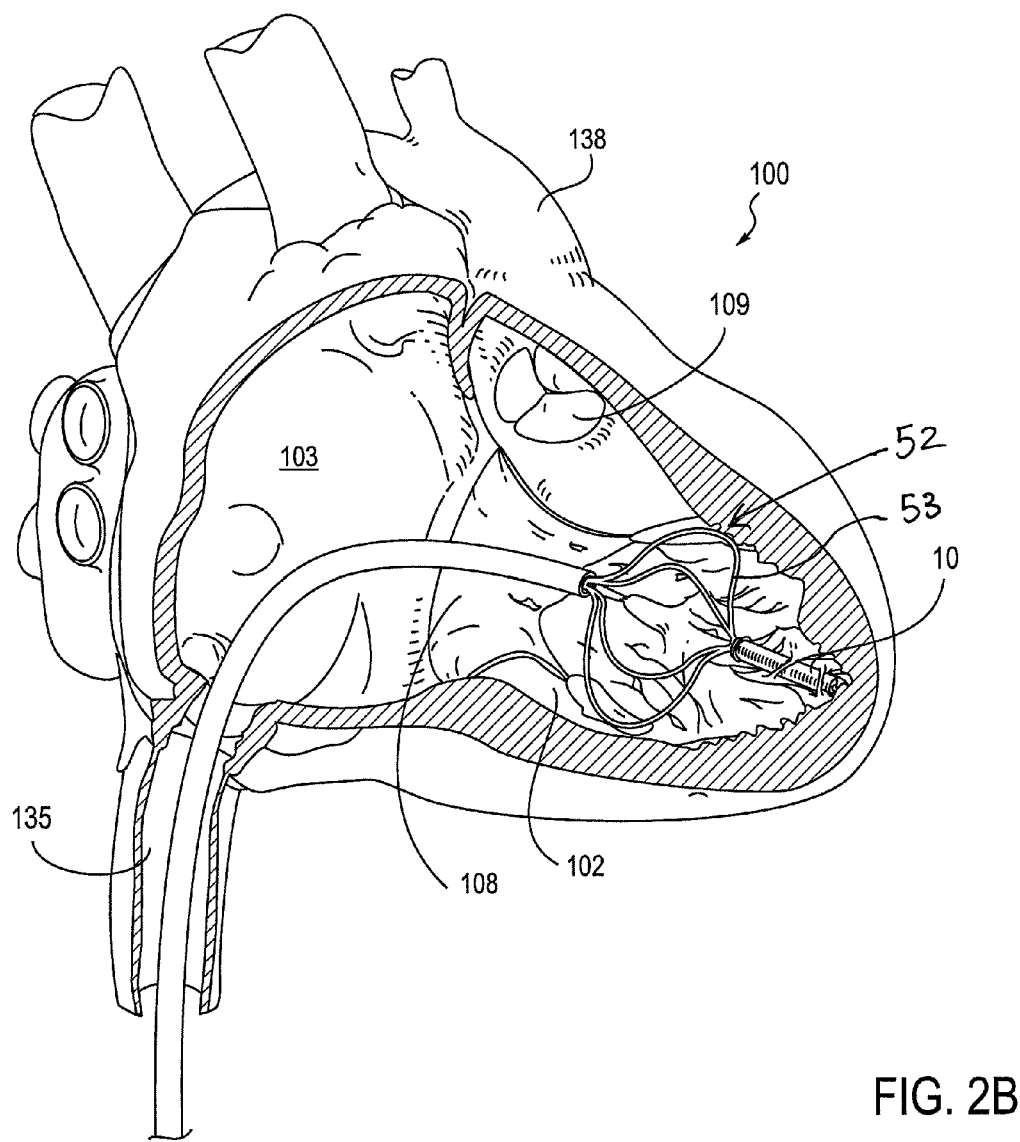
Figure 2C:
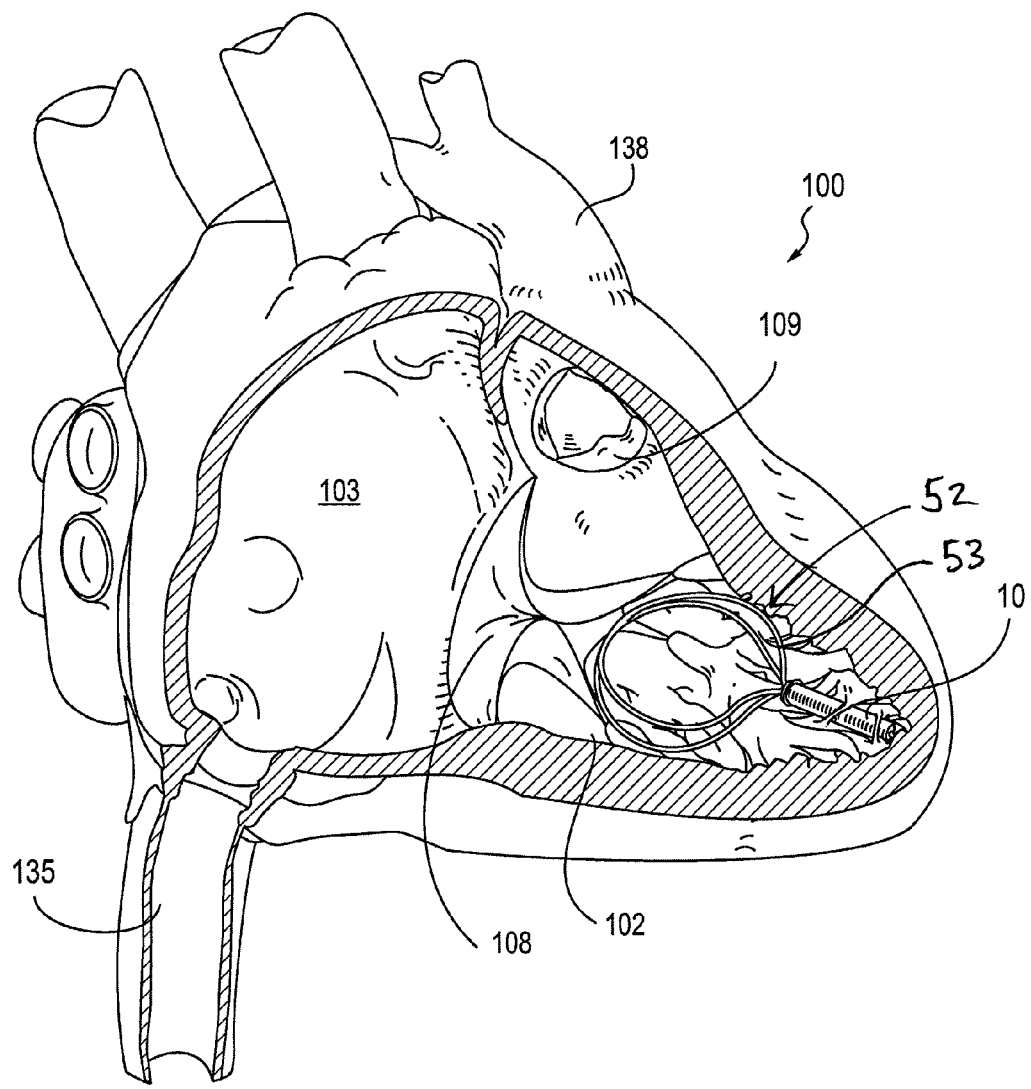

FIGS. 2A-2C show an embodiment of a leadless biostimulator 10 with a proximally-connected expandable structure. In some embodiments, the expandable structure includes Nitinol, which provides the structure a superelastic quality that allows deformation into a constrained configuration and a high-fidelity return to a native configuration upon being released from constraint. FIG. 2A shows the leadless biostimulator being delivered to the right ventricle within a delivery device 200 with the struts of the expandable structure in a compressed linear configuration within the confines of the delivery device. After the device is successfully implanted at a primary fixation site in the right ventricle, the delivery device is withdrawn as it ejects the LBS 10. As shown in FIG. 2B as the expandable structure 52 is released from the constraint provided by the delivery device, the struts 53 return to their native bowed configuration, giving the expandable device as a whole its expanded configuration. As shown in FIGS. 2B-2C, the struts can comprise a looped shape, wherein first and second ends of the struts are attached to the housing of the biostimulator. Although the expandable structure is shown with a plurality of struts in FIGS. 2B-2C, in some embodiments, the expandable structure can comprise a single strut.

Depending on the orientation of the expandable structure 52 within the heart chamber, and the relative dimensions of the structure and the host chamber, the structure may contact the heart chamber wall to varying degree, or it may be disposed in such a way that there is minimal contact with the heart chamber wall. In some cases, the walls of the chamber may compress the expandable structure as the ventricle contracts during a heart beat. This event is depicted in FIG. 2C, which shows the leadless biostimulator as implanted with the right ventricle in a contracted state, the ventricle walls compressing the compliant expandable structure. As the ventricle walls contract, the struts 53, which are highly compliant, compress and do not interfere with the movement of the heart muscle.

Figure 3A:
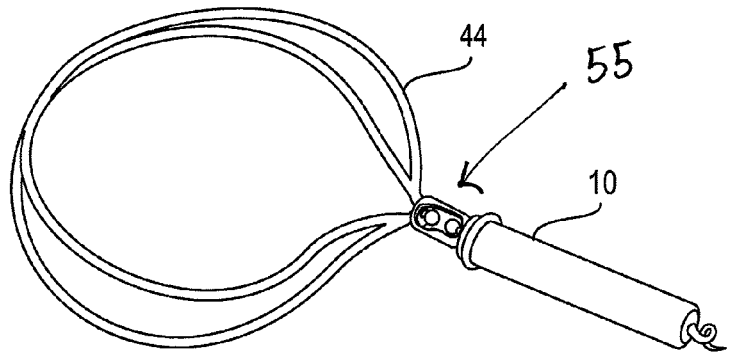
FIGS. 3A and 3B show embodiments of a coupling mechanism that connects an expandable structure to a leadless biostimulator that isolate the LBS from potentially destabilizing force conveyed from the expandable structure to the LBS at its site of primary fixation.
Figure 3B:
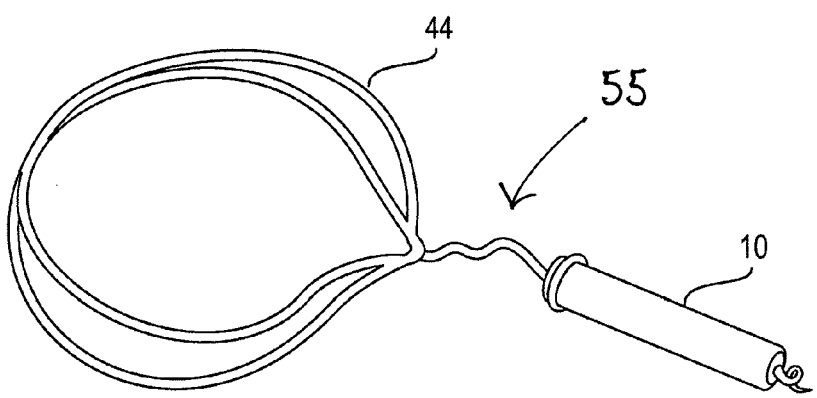
Figure 3C:
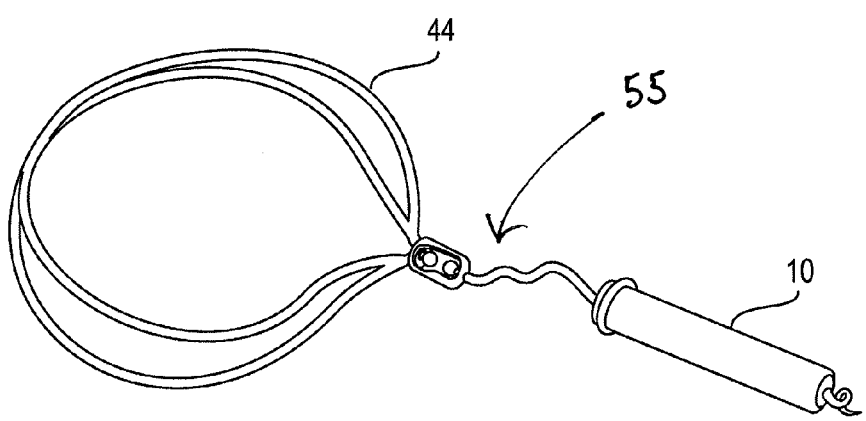
FIG. 3C shows a coupling mechanism that includes a short flexible tether and a swivel mechanism.

FIGS. 3A-3C show details of embodiments of a coupling mechanism 55 that couples the leadless biostimulator 10 and the expandable structure 52 that allows a freedom of movement of the expandable structure with respect to the biostimulator. This freedom of movement provides several advantages to the long term stability of the LBS at its primary implantation site. In one aspect, the freedom of movement isolates or insulates the LBS from destabilizing force that could otherwise be conveyed to it by movement of the coupled expandable structure. In another aspect, the freedom of movement allows the expandable structure to maintain a position within the heart chamber that least interferes with the wall of the heart chamber, and more particularly, least interferes with contraction of the chamber as the heart beats. In yet another aspect, the expandable structure provides a net stabilizing effect on the primary fixation by limiting the movement of the LBS in response to the movement of blood and the movement of the cardiac muscle at the site of fixation to less than it would be absent such a coupled structure.

FIG. 3A shows a coupling mechanism 55 that includes a swivel that allows the expandable structure to rotate within the ventricle to a position where it encounters the least interaction with portions of the ventricle wall. By virtue of the swivel, the LBS is insulated from torque that could otherwise be applied to the LBS at its site of implantation, and which could destabilize the primary fixation. FIG. 3B shows a coupling mechanism 55 that includes a short flexible tether that allows the expandable structure to wobble within the ventricle with respect to the LBS to which it is coupled. Again, the coupling mechanism thus insulates the LBS from destabilizing force from the movement of the expandable structure which could threaten the integrity of the primary fixation. Other embodiments of a coupling mechanism 55 (not shown) may include both tethering and swiveling features. FIG. 3C shows a coupling mechanism that includes a short flexible tether and a swivel mechanism, thus incorporating the features of a swivel and short tether, as just described.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A leadless biostimulator comprising:
   a housing sized and configured to be disposed within a heart chamber of a human;
   a primary fixation element configured to actively affix the biostimulator to a heart wall within the heart chamber; and
   an expandable structure connected to a proximal portion of the housing, the expandable structure being adapted to assume a compressed linear configuration during delivery and an expanded configuration after delivery, wherein the expanded configuration of the expandable structure has a cross-sectional dimension that is greater than a diameter of a vascular exit pathway from the heart chamber so that expansion of expandable structure confines the leadless biostimulator and the expandable structure to the heart chamber.

2. The leadless biostimulator of claim 1 wherein expandable structure comprises a plurality of struts.

3. The leadless biostimulator of claim 2 wherein the plurality of struts comprise a looped shape.

4. The leadless biostimulator of claim 2, wherein the plurality of struts has an asymmetrical bowed configuration such that a greater radial diameter is proximally-skewed.

5. The leadless biostimulator of claim 2, wherein the plurality of struts is configured to compress when the heart chamber contracts during a heart-beat so that the plurality of struts do not interfere with movement of heart muscle of the heart chamber.

6. The leadless biostimulator of claim 1 wherein the heart chamber is a right ventricle of the heart and the vascular exit pathway from the heart chamber is a pulmonic value.

7. The leadless biostimulator of claim 1 wherein the expandable structure comprises nitinol.

8. The leadless biostimulator of claim 1, wherein the expandable structure further comprising a coupling mechanism that couples the housing to the expandable structure to allow for movement of the expandable structure with respect to the housing.

9. The leadless biostimulator of claim 8 wherein the coupling mechanism comprises a swivel, wherein the swivel is configured to insulate the biostimulator from torque when the biostimulator is affixed to the heart wall with the heart chamber.

10. The leadless biostimulator of claim 8 wherein the coupling mechanism comprises a flexible tether.

11. The leadless biostimulator of claim 1, further comprising a coupling mechanism that couples the housing to the expandable structure to allow for movement of the expandable structure with respect to the housing, wherein the coupling mechanism isolates the housing from destabilizing force that could otherwise be conveyed to the housing by movement of the expandable structure.

12. The leadless biostimulator of claim 1, further comprising a one or more soluble coverings configured to encapsulate at least one of the primary fixation element and the secondary fixation element.

13. The leadless biostimulator of claim 1, wherein the one or more soluble coverings is configured to encapsulate the secondary fixation element so that the secondary fixation element is secured in the collapsed linear configuration.

14. The leadless biostimulator of claim 1, wherein the expandable structure has a stiffness configured to prevent the biostimulator from turning or reorienting within the heart chamber when the biostimulator is dislodged from the heart wall.

15. The leadless biostimulator of claim 1, wherein the heart chamber is a right ventricle of the heart and the vascular exit pathway from the heart chamber is a pulmonic artery.

16. The leadless biostimulator of claim 1, wherein the heart chamber is a right ventricle of the heart and the vascular exit pathway from the heart chamber is a semilunar valve, and wherein the expanded configuration of the expandable structure is configured not to pass through the semilunar valve so that the biostimulator does not enter the pulmonary artery.

17. A method of retaining a leadless biostimulator within a human heart of a patient, comprising:
   confining an expandable member of the leadless biostimulator within a delivery device;
   delivering the leadless biostimulator to a heart chamber with the delivery device;
   actively affixing a primary fixation element of the leadless biostimulator to a heart wall of the heart chamber; and
   expanding the expandable member within the heart chamber to have a cross-sectional linear dimension greater than a downstream vascular exit from the heart chamber such that the expandable member is confined to the heart chamber and the leadless biostimulator is confined to the heart chamber by the expandable member.

18. The method of claim 17 wherein the heart chamber is a right ventricle of the heart and wherein the downstream vascular exit from the heart chamber is pulmonary artery.

19. The method of claim 17, wherein expanding the expandable member within the heart comprises bowing struts of the expandable member from a linear configuration to a bowed configuration.

* * * * *